United States Patent [19]
Connor et al.

[11] 3,973,020
[45] Aug. 3, 1976

[54] 3-(2-PYRIDINYL)-4(1H)-CINNOLINONE N-OXIDES

[75] Inventors: David T. Connor, Parsippany; Patricia A. Young, Madison; Maximilian von Strandtmann, Rockaway Township, all of N.J.

[73] Assignee: Warner-Lambert Company, Morris Plains, N.J.

[22] Filed: Sept. 8, 1975

[21] Appl. No.: 611,120

[52] U.S. Cl. .......................... 424/250; 260/250 C; 260/296 B
[51] Int. Cl.² ............... A61K 31/495; C07D 237/28
[58] Field of Search ............... 424/250; 260/250 C

[56] References Cited
OTHER PUBLICATIONS
Morley et al. Chem Abs. 54, 7715a (1959).

*Primary Examiner*—Alton D. Rollins
*Assistant Examiner*—Mark L. Berch
*Attorney, Agent, or Firm*—Albert H. Graddis; Frank S. Chow; Anne M. Kelly

[57] ABSTRACT

3-(2-Pyridinyl)-4(1H)-cinnolinone N-oxides of the formula I:

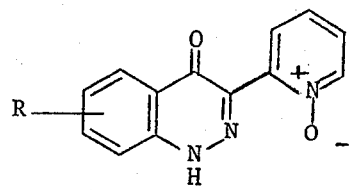

wherein R is hydrogen, halogen, lower alkyl, hydroxy or alkoxy; the pharmaceutically acceptable acid addition salts thereof; and a process for the preparation thereof, are described. The compounds of the invention are useful for the treatment of hyperacidity.

4 Claims, No Drawings

3-(2-PYRIDINYL)-4(1H)-CINNOLINONE N-OXIDES

DESCRIPTION OF THE PRIOR ART

Osborne et al., in J. Heterocyclic Chem. 1: 138–140 (1964), describe the preparation of 1-phenyl-2-(pyridinyl)ethanone N-oxide, using sodium amide in liquid ammonia as the condensing agent. No pharmacological activity is reported for this or related compounds described by Osborne et al.

DESCRIPTION OF THE PARTICULAR EMBODIMENTS

This invention relates to a compound having the formula I:

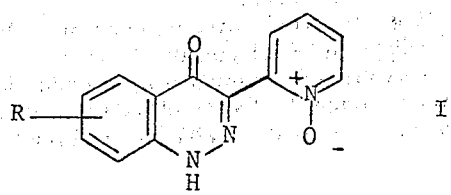

wherein R is hydrogen, halogen, lower alkyl, hydroxy, or alkoxy; and the pharmaceutically acceptable acid addition salts thereof. Compounds of the invention having formula I, wherein R is hydrogen, are particularly preferred.

The compounds of the invention are prepared by reacting a compound having the formula II:

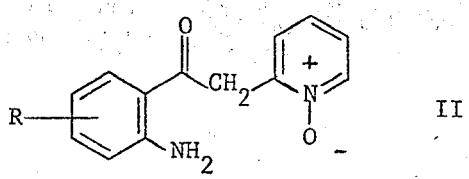

wherein R is as defined in compound I, with sodium nitrite in the presence of a mineral acid, such as hydrochloric acid, at reduced temperatures, typically at about 15°C. Ring closure is effected and a compound having formula I is obtained.

The starting materials II used to obtain the compounds of the invention are prepared as described in co-pending Application Ser. No. 611,282, filed Sept.8, 1975, now pending. Thus, compounds of the formula II are prepared by reacting an N-substituted isatoic anhydride having the formula III:

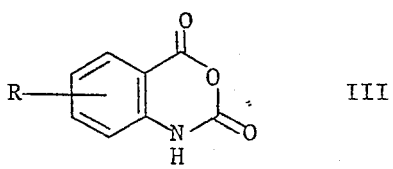

wherein R is as defined above in compound II with a 2-picoline N-oxide of the formula IV:

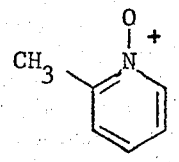

The above reaction is conducted in liquid ammonia in the presence of an alkali metal amide condensing agent such as sodium, potassium or lithium amide (sodium amide preferred).

Representative starting materials having the formula II which may be prepared by the above-described reaction include: 1-[2-aminophenyl]-2-(2-pyridinyl)ethanone N-oxide, 1-[4-chloro-2-aminophenyl]-2-(2-pyridinyl)ethanone N-oxide, 1-[5-hydroxy-2-aminophenyl]-2-(2-pyridinyl)ethanone N-oxide, 1-[5-methyl-2-aminophenyl]-2-(2-pyridinyl)ethanone N-oxide and 1-[3-methoxy-2-aminophenyl]-2-(2-pyridinyl)ethanone N-oxide.

Pharmaceutically acceptable acid addition salts of the compound of this invention are prepared according to conventional procedures by treating the free base form of the compounds of the invention in an alcohol solution with the desired acid.

In the above formulas for the compounds of the invention, the R group definitions may be more fully described as follows: the term "lower alkyl" is meant to include lower aliphatic hydrocarbons having 1 to 7, preferably 1 to 4 carbon atoms in the alkyl chain, such as methyl, ethyl, propyl, isopropyl, butyl or isobutyl. This definition for lower alkyl also applies to the alkyl portions of "alkoxy". The term "halogen" is meant to include bromine, chlorine, iodine and fluorine.

The compounds of this invention having formula I exhibit gastric anti-secretory activity when tested according to the procedure described by H. Shay et al., Gastroenterology, 5: 43 (1945). In this last-mentioned test, male Long Evans Hooded rats (150–200 gms.) are fasted for 24 hours prior to testing (water ad lib). Rats are randomly divided into groups of 5 rats each and housed individually. At the time of testing, each rat is lightly anesthetised with ether, its stomach exposed through a midline abdominal incision and the pylorus ligated with silk thread. The incision is sutured, closed and covered with Flexible Collodion, U.S.P. to prevent ingestion of blood. Test compound or vehicle control is administered (a) intraduodenally prior to closing the incision; (b) intraperitoneally immediately after ligation; or (c) orally as a one hour pretreatment. Four hours later, the rats are sacrificed by ether and their stomachs removed and opened.

Gastric contents are placed in centrifuge tubes and centrifuged to remove debree. The volume of gastric juice is measured (expressed in milliliters) and titratable acidity determined electrometrically to pH 7.4 (expressed as milliequivalents of acid per liter). Results are expressed as percent reduction of volume and/or titratable acidity from control groups average. Reduced gastric acid secretion in experimental animals in the above-described test is considered to be representative of pharmacological utility in the treatment of hyperacidity in humans.

Thus, the compounds of the invention are active in the treatment of hyperacidic conditions when administered to mammals at a dose level of from about 20 to about 50 mg/kg of body weight by the oral or parenteral route. This dosage may be varied depending on the severity of the condition, the age, weight, sex and class of mammal being treated, as well as the route of administration. For example, when 3-(2-pyridinyl)-4(1H)-cinnolinone N-oxide (the compound of Example 1) is tested in the pylorus ligated rat in the above-described procedure at a dose of about 20 mg/kg, intraperitoneally, a reduction of about 38.4% in volume of gastric acid was obtained, compared to controls.

In use, the compounds of the invention may be combined with parenterally acceptable vehicles, such as gum tragacanth in saline suspension, to provide dosage forms suitable for parenteral administration; or they may be combined with pharmaceutical diluents such as lactose, cornstarch, and the like and formulated into tablet or capsule dosage forms.

To further illustrate the practice of this invention, the following examples are included:

EXAMPLE 1

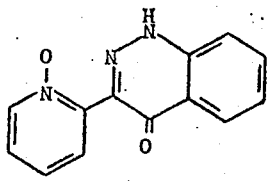

3-(2-Pyridinyl)-4(1H)-Cinnolinone N-Oxide

1 N hydrochloric acid (10.5 ml), cooled to 15°C., is added to a solution of 1-[2-aminophenyl]-2-(2-pyridinyl)-ethanone N-oxide (2.0 g) in water (40 ml) at 5°C. Maintaining 5°C., a cooled solution of sodium nitrite (0.726 g) in water (6 ml) is slowly added. The mixture is allowed to come to 20°C. and stirred for 20 minutes. The product is filtered off and washed in succession with water, isopropanol, and ethyl ether. Recrystallization from N,N-dimethylformamide gives white crystals (1.33 g, 63.5%), m.p. dec. > 315°C.

Mass Spectrum: observed molecular weight 239.0632; calculated for $C_{13}H_9N_3O_2$ 239.0695.

We claim:
1. A compound of the formula I:

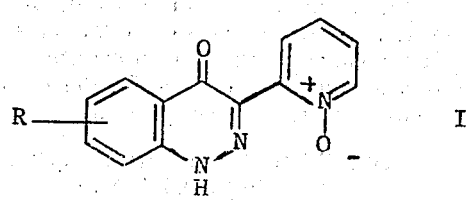

wherein R is hydrogen, halogen, lower alkyl, hydroxy or alkoxy; and the pharmaceutically acceptable acid addition salts thereof.

2. A compound according to claim 1 which is 3-(2-pyridinyl)-4(1H)-cinnolinone N-oxide.

3. A method for treating hyperacidity in mammals which comprises the administration of a sufficient amount of a compound having the formula I:

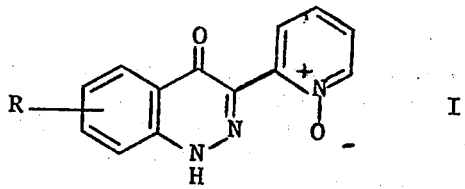

wherein R is hydrogen, halogen, lower alkyl, hydroxy or alkoxy.

4. A method according to claim 3 wherein 3-(2-pyridinyl)-4(1H)-cinnolinone N-oxide is administered.

* * * * *